US012797242B2

(12) United States Patent
Arba Mosquera et al.

(10) Patent No.: US 12,797,242 B2
(45) Date of Patent: Nov. 17, 2026

(54) METHOD FOR PROVIDING CONTROL DATA FOR A PROCESSING DEVICE, METHOD FOR CONTROLLING A PROCESSING DEVICE, CONTROL DEVICE, PROCESSING DEVICE, COMPUTER PROGRAM AND COMPUTER-READABLE MEDIUM

(71) Applicant: SCHWIND EYE-TECH-SOLUTIONS GMBH, Kleinostheim (DE)

(72) Inventors: Samuel Arba Mosquera, Aschaffenburg (DE); Mario Shraiki, Ober-Ramstadt (DE); Nico Triefenbach, Mainaschaff (DE)

(73) Assignee: SCHWIND EYE-TECH-SOLUTIONS GMBH, Kleinostheim (DE)

( * ) Notice: Subject to any disclaimer, the term of this patent is extended or adjusted under 35 U.S.C. 154(b) by 133 days.

(21) Appl. No.: 18/583,074

(22) Filed: Feb. 21, 2024

(65) Prior Publication Data

US 2024/0277525 A1 Aug. 22, 2024

(30) Foreign Application Priority Data

Feb. 22, 2023 (DE) ..................... 10 2023 104 353.6

(51) Int. Cl.

*A61F 9/00* (2006.01)
*A61F 9/008* (2006.01)
*G16H 40/63* (2018.01)
*A61B 18/00* (2006.01)

(52) U.S. Cl.

CPC ............. *A61F 9/008* (2013.01); *G16H 40/63* (2018.01); *A61B 2018/00678* (2013.01); *A61B 2018/00684* (2013.01); *A61B 2018/00702* (2013.01); *A61B 2018/00732* (2013.01); *A61B 2018/00761* (2013.01); *A61F 2009/00872* (2013.01)

(58) Field of Classification Search

None
See application file for complete search history.

(56) References Cited

FOREIGN PATENT DOCUMENTS

| | | | |
|---|---|---|---|
| DE | 10 2021 210 661 | A1 | 3/2023 |
| EP | 2 445 461 | B1 | 5/2012 |
| EP | 4 079 267 | A1 | 10/2022 |
| WO | 2011069516 | A1 | 6/2011 |

OTHER PUBLICATIONS

Office Action issued Sep. 23, 2024 in DE Appl. No. 10 2023 104 353.6.

*Primary Examiner* — Sana Sahand
(74) *Attorney, Agent, or Firm* — MEDLER FERRO WOODHOUSE & MILLS PLLC

(57) ABSTRACT

A method for providing control data for a processing device with at least one laser and with at least one focusing optics is provided. The method comprises the following steps performed by a control device: receiving a specification for processing a material of an object in at least one preset separation point in a respective, preset separation depth of the material; ascertaining a respective focusing depth of a focusing point to be adjusted in the focusing optics of the processing device for separating the material in the respective, at least one preset separation point in the preset separation depth of the material; providing control data, wherein the control data is configured for controlling the focusing optics of the processing device for focusing at least one laser pulse on the at least one focusing point in the focusing depth of the material to be adjusted and for controlling the laser.

21 Claims, 4 Drawing Sheets

METHOD FOR PROVIDING CONTROL DATA FOR A PROCESSING DEVICE, METHOD FOR CONTROLLING A PROCESSING DEVICE, CONTROL DEVICE, PROCESSING DEVICE, COMPUTER PROGRAM AND COMPUTER-READABLE MEDIUM

FIELD

The present invention relates to a method for providing control data for a processing device with at least one laser and with at least one focusing optics, according to the embodiments presented herein. In addition, the invention relates to a method for controlling a processing device according to the embodiments presented herein, to a control device according to the embodiments presented herein, to a processing device according to the embodiments presented herein, to a computer program according to the embodiments presented herein and to a computer-readable medium according to the embodiments presented herein.

BACKGROUND

Processing devices for laser-based processing an object are known from the prior art and are for example employed in the surface processing of objects of metal. In objects of optically transparent materials, a laser-based material processing may be effected by inducing an optical breakthrough in the material. For inducing the optical breakthrough, energy may be provided by laser pulses in a predetermined place until a formation of a cavitation bubble occurs in the place. It causes separating or cutting the material.

A further field of application of the processing devices for laser-based processing is the medical technology. In the medical technology, the laser-based processing devices are applied as treatment apparatuses for example for correcting an optical visual disorder and/or pathologically and/or unnaturally altered areas of the cornea. Therein, a pulsed laser and a beam focusing device may for example be formed such that laser pulses effect a photodisruption and/or photoablation due to the optical breakthrough in a focus situated within an organic tissue, to remove a tissue, in particular a tissue lenticule, from the cornea.

Therein, a pulsed laser and a beam focusing device may for example be formed such that laser pulses exceed a certain threshold value with respect to an energy or an energy density and/or a power or a power density in a focus situated within the organic tissue, to effect a certain reaction in the tissue. This approach is for example applied in the so-called crosslinking method (CXL), wherein a photochemical reaction of riboflavin is caused by UV radiation. This photochemical reaction results in crosslinking of the corneal collagen, whereby crosslinks form in the stroma of the lens. Furthermore, the LIRIC (Laser-Induced Refractive Index Change) method is also based on exceeding a threshold value, to change a refractive index of the corneal tissue without a surgical intervention. However, it has to be ensured therein that a threshold value, which would result in a damage of the corneal tissue, is not exceeded. In the photodisruption, the photoablation and the plasma mediated ablation, a threshold value for decomposition of the tissue is specifically exceeded by focusing laser pulses to remove a tissue, in particular a tissue lenticule, from the cornea.

Widespread methods for laser treatment of the cornea like the photodisruption and/or the photoablation are based on specifically inducing the optical breakthrough in the corneal tissue by the pulsed laser. The optical breakthrough describes a strong local ionization of the corneal tissue, wherein a critical plasma density is exceeded. The optical breakthrough may be initiated in laser-induced manner in the corneal tissue in that a power density threshold is exceeded by the laser pulse within the corneal tissue. For this purpose, the laser pulse is focused on a focusing point in the corneal tissue, in which it then has a maximum power density, which exceeds the power density threshold. Upon exceeding the critical plasma density, the local absorption capacity of the corneal tissue rises, whereby the plasma temperature is severely increased. Due to the temperature increase of the plasma, a Coulomb expansion of the plasma occurs, whereby a cavitation bubble arises in the corneal tissue, in which the corneal tissue is severed. By focusing laser pulses on the predetermined focusing points, it is thereby possible to sever the corneal tissue in specific and locally limited manner in the focusing points. The photodisruption is based on a local mechanical decomposition of the corneal tissue, which is caused by a shock wave arising in the optical breakthrough.

For limiting the tissue influences caused by the optical breakthrough to predetermined separation points in a predetermined separation depth, it has to be ensured that the power density threshold is exceeded in the focusing points in the predetermined separation depth. Exceeding the power density threshold by the laser pulse before it has penetrated into the predetermined separation depth, results in the beginning of the tissue decomposition in a breakthrough depth, which deviates from the separation depth. Thereby, an undesired separation of the corneal tissue outside of the separation depth may finally occur. The same problem also arises in the cited LIRIC and CXL methods. Exceeding the threshold value results in a change of the tissue in an incorrect depth in these methods.

According to the prior art, it is therefore usual to calibrate processing devices such that a preset power density threshold is exceeded in the focusing point of the laser beam. The focusing depth of the focus is adjusted during processing such that it coincides with the adjusted separation depth or the adjusted processing depth.

However, the assumption idealized in inducing the optical breakthrough that the material or tissue decomposition is restricted to an area around the focusing point, is only acceptable if the preset power density threshold assumed in the calibration coincides with an actual power density threshold. However, the power density threshold, from which a beginning of the plasma ignition in the material occurs, is not constant, but depends both on the laser and on local material characteristics. The power density threshold is for example influenced by a pulse duration of the laser pulse and/or an adjusted numerical aperture of the laser pulse. Besides, a dependency of the power density threshold on the absorption capacity of the local material arises. Therein, the material may have respective characteristics depending on the depth, which have to be taken into account in ascertaining the breakthrough depth. If the material is corneal tissue, there are laterally relatively low differences between different areas of the corneal tissue.

In the calibration, a further problem arises in current processing devices due to a new approach in the energy selection of a laser pulse. The energy of the pulse may generally be preset within a certain range by the user of the processing device. Formerly, a relatively high energy value was preset for a laser pulse. Compared thereto, effects of local variations on the position of separation depth were relatively low and often negligible. In newer processing devices, lower energies are often selected for the laser pulses. Herein, variations have a more severe effect. Herein, a previously usual calibration by an adaptation of a target depth to an actual depth is not possible in unrestricted manner.

The optical breakthrough in the material may also be initiated upon exceeding a power threshold, an energy density or an energy density threshold, which then represent a disruption threshold to be exceeded.

The dependencies of the disruption thresholds on parameters of the laser and/or of the local material are for example described in the following scientific publications with respect to corneal tissues:

Franco Docchio, Pietro Regondi, Malcolm R. C. Capon, and John Mellerio, "Study of the temporal and spatial dynamics of plasmas induced in liquids by nanosecond Nd: YAG laser pulses. 1: Analysis of the plasma starting times," Appl. Opt. 27, 3661-3668 (1988)

Franco Docchio, Pietro Regondi, Malcolm R. C. Capon, and John Mellerio, "Study of the temporal and spatial dynamics of plasmas induced in liquids by nanosecond Nd: YAG laser pulses. 2: Plasma luminescence and shielding," Appl. Opt. 27, 3669-3674 (1988)

An assumption of a preset power density threshold deviating from the real power density threshold may result in the fact that the power density threshold is exceeded in a lower depth than the focusing depth. Thereby, a deviation between the real separation plane and the preset separation plane occurs despite of a calibration.

SUMMARY

It is an object of the invention to provide a solution, which ensures processing a material, in particular separating the material, by a method based on an optical breakthrough in a predetermined depth. In particular, it is an object of the invention to minimize deviations of the separation depth, which due to variations in the current energy ranges.

This object is solved by the method according to the invention according to the embodiments presented herein, the method according to the invention according to the embodiments presented herein, the control device according to the invention according to the embodiments presented herein, the processing device according to the invention according to the embodiments presented herein, the computer program according to the invention according to the embodiments presented herein and the computer-readable medium according to the invention according to the embodiments presented herein. Advantageous configurations with convenient embodiments of the invention are specified in the respective dependent claims, wherein advantageous configurations of the method are to be regarded as advantageous configurations of the control device, of the processing device, of the computer program and of the computer-readable medium and vice versa.

A first aspect of the invention relates to a method for providing control data for a processing device with at least one laser and with at least one focusing optics, wherein the method comprises the following steps performed by a control device.

In a first step, receiving a specification for processing, in particular for separating a material of an object, for example by a method based on an optical breakthrough in at least one preset separation point in a respective separation depth of the material is effected. The separation depth may also describe a processing depth, in which the material is processed but not separated according to the specification. In other words, the specification is received by the control device, which instructs the control device to control the processing device in order that the material is processed, in particular separated, in the at least one preset separation point in the method. The method may be a method based on an optical breakthrough, for example a photodisruption method. Therein, the at least one separation point is arranged in a respective, preset separation depth in the material. The preset separation depth may describe a distance of the respective separation point from a surface of the material, which faces the processing device during processing.

By the control device, a focusing depth of a respective focusing point to be adjusted in the focusing optics of the processing device for separating the material in the respective separation point in the preset separation depth is ascertained. In other words, a respective focusing point of a respective focusing depth is ascertained by the control device, on which a laser pulse output by the laser is to be focused by the focusing optics of the processing device in order that the material is separated in the respective at least one separation point in the separation depth. The focusing point and the focusing depth may be ascertained such that the separation depth is at an end of a bubble, which may arise by the optical breakthrough in the focusing point, or in a center of the said bubble. The end of the bubble may face or face away from a top side of the material and coincide with a minimum depth of the bubble or a maximum depth of the bubble. The center of the bubble may be in a central depth of the bubble.

After ascertaining the respective focusing point of the respective focusing depth, an output of the control data for controlling the focusing optics of the processing device for focusing the at least one laser pulse on the respective focusing point in the focusing depth of the material to be adjusted is effected. In other words, the focusing optics of the processing device is controlled by the control data such that the focusing optics is adjusted to focus the at least one laser pulse guided by the focusing optics to the respective focusing point in the focusing depth of the material to be adjusted.

It is provided that the focusing depth of the respective focusing point to be adjusted is ascertained according to a predetermined adaptation method depending on an ascertained breakthrough parameter threshold, at least one laser parameter and/or at least one material parameter. The breakthrough parameter threshold describes a threshold value of a breakthrough parameter, for example of a power density, from which a breakthrough reaction of the material begins. In other words, the focusing depth of the respective focusing point is ascertained according to the predetermined adaptation method, wherein the focusing depth depends on the breakthrough parameter threshold, above which the disruption of the material begins. The focusing depth is ascertained by the adaptation method also depending on the at least one laser parameter and/or the at least one material parameter. In other words, the focusing depth to be adjusted depends on the at least one laser parameter and/or the at least one material parameter. The at least one laser parameter may for example include an energy and/or a numerical aperture of the at least one laser pulse, whereby a course of the breakthrough parameter of the at least one laser pulse over a penetration depth of the at least one laser pulse in the material may be ascertained. For ascertaining the course of the breakthrough parameter of the at least one laser pulse, a conical course or a Gaussian course of a cross-section of the laser pulse may be approximatively assumed.

Additionally or alternatively to the at least one laser parameter, the at least one material parameter may be taken into account for ascertaining the focusing depth in the predetermined adaptation method. The at least one material parameter may for example include an absorption capacity of the material, a water portion of the material, an expansion state of the material and/or a density of the material. The at least one material parameter may depend on the depth. Thereby, it may be taken into account that characteristics of the local material in particular depend on the depth, in which the local material is located.

According to the adaptation method, the focusing depth is ascertained by the control device, to which the focusing optics is to be adjusted in order that the breakthrough parameter threshold is exceeded by the breakthrough parameter of the at least one laser pulse in the preset separation depth. In other words, it is provided that the at least one laser pulse is focused on the focusing point in the focusing depth by the focusing optics, wherein the focusing depth is adjusted such that the breakthrough reaction, which causes the material decomposition of the material, begins in the preset separation depth of the material and continues in the depth below the separation depth. The focusing depth may for example be adjusted such that the beam diameter of the at least one laser pulse decreasing with increasing penetration depth has a beam diameter in the separation depth, which results in exceeding a power density threshold as the breakthrough parameter threshold by the power density as the breakthrough parameter of the at least one laser pulse at a preset power density of the at least one laser pulse.

By the adaptation of the focusing depth depending on the at least one laser parameter and/or the at least one material parameter, deviations of the breakthrough depth from the adjusted separation depth may be minimized. Thereby, the advantage arises that an accuracy of the separation depth in the separation of the material is increased.

The control data may include a respective dataset for positioning and/or for focusing individual laser pulses in the material. Additionally or alternatively, a respective dataset for adjusting at least one beam device for beam guidance and/or beam shaping and/or beam deflection and/or beam focusing of a laser beam of the respective laser may be included in the control data.

The invention also includes embodiments, by which additional advantages arise.

A further embodiment of the invention provides that the material is a corneal tissue of a human or animal eye. In other words, the method is provided for treating a cornea of a human or animal eye.

A further embodiment of the invention provides that the focusing depth is selected such that the focusing depth is different from the separation depth, and the breakthrough parameter of the at least one laser pulse is identical to the ascertained breakthrough parameter threshold in the preset separation depth.

A further embodiment of the invention provides that the breakthrough parameter threshold is ascertained by the control device according to a threshold value ascertaining method depending on the at least one preset laser parameter and/or the at least one material parameter. In other words, it is provided that the breakthrough parameter threshold is not constantly preset, but is ascertained by the control device depending on the at least one preset laser parameter and/or the at least one material parameter. By the embodiment, the advantage arises that the dependency of the breakthrough parameter threshold on the laser and the material is taken into account. Thus, a more accurate adjustment of the focusing depth is possible than it is possible in case of assumption of a preset value of the breakthrough parameter threshold. For example, it may be provided that the breakthrough parameter threshold is ascertained depending on a pulse duration of the laser pulse and/or an absorption coefficient of the material. Thereby, the at least one laser parameter and/or the at least one material parameter may be taken into account both in ascertaining the course of the laser pulse and in determining the breakthrough parameter threshold.

A further embodiment of the invention provides that the breakthrough parameter describes a local power of the at least one laser pulse and the breakthrough parameter threshold describes a power threshold of the at least one laser pulse, from which a breakthrough reaction of the material begins. In other words, the breakthrough parameter is the local power, which the laser pulse has in a certain penetration depth in the tissue, or the local power, which is absorbed by the material in the certain depth. The power may relate to a maximum power, an average power or a minimum power of the power course of the at least one laser pulse. Accordingly, the power threshold may describe the local power, which causes a breakthrough reaction of the material.

A further embodiment of the invention provides that the breakthrough parameter describes a local power density of the at least one laser pulse and the breakthrough parameter threshold describes a power density threshold of the at least one laser pulse, from which a breakthrough reaction of the material begins. In other words, the breakthrough parameter is the local power density, which the laser pulse has in a certain penetration depth in the tissue, or the local power density, which is absorbed by the material in the certain depth. The power density may relate to a maximum power density, an average power density or a minimum power density of a power density course of the at least one laser pulse. Accordingly, the power density threshold may describe the local power density, which causes a breakthrough reaction of the material.

A further embodiment of the invention provides that the breakthrough parameter describes a local energy of the at least one laser pulse and the breakthrough parameter threshold describes an energy threshold of the at least one laser pulse, from which a breakthrough reaction of the material begins. In other words, the breakthrough parameter is the local energy, which the laser pulse has in a certain penetration depth in the tissue, or the local energy, which is absorbed by the material in the certain depth. The energy may relate to a maximum energy, an average energy or a minimum energy of an energy course of the at least one laser pulse. Accordingly, the energy threshold may describe the local energy, which causes a breakthrough reaction of the material.

A further embodiment of the invention provides that the breakthrough parameter describes a local energy density of the at least one laser pulse and the breakthrough parameter threshold describes an energy density threshold of the at least one laser pulse, from which a breakthrough reaction of the material begins. In other words, the breakthrough parameter is the local energy density, which the laser pulse has in a certain penetration depth in the tissue, or the local energy density, which is absorbed by the material in the certain depth. The energy density may relate to a maximum energy density, an average energy density or a minimum energy density of an energy density course of the at least one laser pulse. Accordingly, the energy density threshold may describe the local energy density, which causes a breakthrough reaction of the material.

A further embodiment of the invention provides that the at least one laser parameter of the at least one laser pulse includes a pulse energy of the at least one laser pulse. In other words, the at least one laser parameter describes the pulse energy of the laser pulse.

A further embodiment of the invention provides that the at least one laser parameter includes a numerical aperture of the at least one laser pulse. Thereby, the advantage arises that a breakthrough parameter course of the at least one laser pulse may be ascertained depending on the numerical aperture.

A further embodiment of the invention provides that the at least one laser parameter includes a wavelength of the at least one laser pulse. In other words, the at least one laser parameter includes the wavelength, which the at least one laser pulse has. Thereby, the advantage arises that effects depending on wavelength with respect to the breakthrough parameter threshold may be taken into account in ascertaining the focusing depth.

A further embodiment of the invention provides that the at least one laser parameter includes a pulse duration of the at least one laser pulse. In other words, the at least one laser parameter comprises the duration of the at least one laser pulse, with which the material is irradiated by the at least one laser pulse.

A further embodiment of the invention provides that the at least one laser parameter of the at least one laser pulse includes a pulse frequency of consecutive laser pulses. In other words, the at least one laser parameter includes a frequency, with which the laser pulses are emitted.

A further embodiment of the invention provides that the at least one material parameter includes an absorption capacity of the material. In other words, it is described by the at least one material parameter, which absorption coefficient the material, through which the laser pulse is guided, has.

A further embodiment of the invention provides that the adaptation method includes ascertaining the focusing depth of the focusing point by a conversion table. In other words, the focusing depth of the focusing point is ascertained by the control device involving the conversion table, which is also referred to as look-up table. The conversion table may include respective focusing depths for preset separation depths, laser parameters and/or material parameters, which may be stored in a storage unit of the control device. Thereby, the advantage arises that a current computing effort of ascertaining the focusing depth may be reduced because the respective focusing depths have already been ascertained in advance.

A further embodiment of the invention provides that the adaptation method includes ascertaining the focusing depth of the focusing point by a fit function. In other words, the fit function is applied by the control device in the adaptation method to ascertain the focusing depth of the focusing point. For example, a certain number of focusing depths for respective separation depths, laser parameters and/or material parameters may be known, to which the fit function may be approximated. By the embodiment, the advantage arises that a calculation of the focusing depth may be effected based on simulated or experimentally ascertained values.

A further embodiment of the invention provides that the adaptation method includes ascertaining the focusing depth of the focusing point by a model. In other words, a model and/or a simulation are applied by the control device for ascertaining the focusing depth of the focusing point to ascertain the focusing depth.

A further aspect of the invention relates to a method for controlling a processing device. Therein, the method includes the method steps of at least one embodiment of a method as it was previously described. Furthermore, the method for controlling the processing device also includes the step of transferring the provided control data to the processing device with at least one laser and at least one focusing optics. The processing device, in particular the laser and the focusing optics, may then be controlled with the control data.

The respective methods may include at least one additional step, which is executed if and only if an application case or an application situation occurs, which has not been explicitly described here. For example, the step may include the output of an error message and/or the output of a request for inputting a user feedback. Additionally or alternatively, it may be provided that a default setting and/or a predetermined initial state are adjusted.

A further aspect of the invention relates to a control device, which is formed to perform the steps of at least one embodiment of one or both of the previously described methods. Thereto, the control device may comprise a computing unit for electronic data processing such as for example a processor. The computing unit may include at least one microcontroller and/or at least one microprocessor. The computing unit may be configured as an integrated circuit and/or microchip. Furthermore, the control device may include an (electronic) data memory or a storage unit. A program code may be stored on the data memory, by which the steps of the respective embodiment of the respective method are encoded. The program code may include the control data for the respective laser. The program code may be executed by the computing unit, whereby the control device is caused to execute the respective embodiment. The control device may be formed as a control chip or control unit. The control device may for example be encompassed by a computer or computer cluster.

A further aspect of the invention relates to a processing device with at least one laser, at least one focusing optics and at least one control device, which is formed to perform the steps of at least one embodiment of one or both of the previously described methods. The respective laser may be formed to at least partially separate a predefined material volume with predefined interfaces of an object by photodisruption and/or to ablate layers of the material by ablation and/or to effect a laser-induced material change in the material.

A further aspect of the invention relates to a computer program. The computer program includes commands, which for example form a program code. The program code may include at least one control dataset with the respective control data for the respective laser. Upon execution of the program code by a computer or a computer cluster, it is caused to execute the previously described method or at least one embodiment thereof.

A further aspect of the invention relates to a computer-readable medium (storage medium), on which the above mentioned computer program and the commands thereof, respectively, are stored. For executing the computer program, a computer or a computer cluster may access the computer-readable medium and read out the content thereof. The storage medium is for example formed as a data memory, in particular at least partially as a volatile or a non-volatile data memory. A non-volatile data memory may be a flash memory and/or an SSD (solid state drive) and/or a hard disk. A volatile data memory may be a RAM (random access memory). For example, the commands may be present as a source code of a programming language and/or as assembler and/or as a binary code.

Further features and advantages of one of the described aspects of the invention may result from the embodiments of another one of the aspects of the invention. Thus, the features of the embodiments of the invention may be present in any combination with each other if they have not been explicitly described as mutually exclusive.

BRIEF DESCRIPTION OF THE DRAWINGS

In the following, additional features and advantages of the invention are described in the form of advantageous execution examples based on the figures. The features or feature combinations of the execution examples described in the following may be present in any combination with each other and/or the features of the embodiments. This means, the features of the execution examples may supplement and/or replace the features of the embodiments and vice versa. Thus, configurations are also to be regarded as encompassed and disclosed by the invention, which are not explicitly shown or explained in the figures, but arise from and may be generated by separated feature combinations from the execution examples and/or embodiments. Thus, configurations are also to be regarded as disclosed, which do not comprise all of the features of an originally formulated claim or extend beyond or deviate from the feature combinations set forth in the relations of the claims. To the execution examples, there shows:

In the figures, identical or functionally identical elements are provided with the same reference characters.

DETAILED DESCRIPTION

Figure 1:
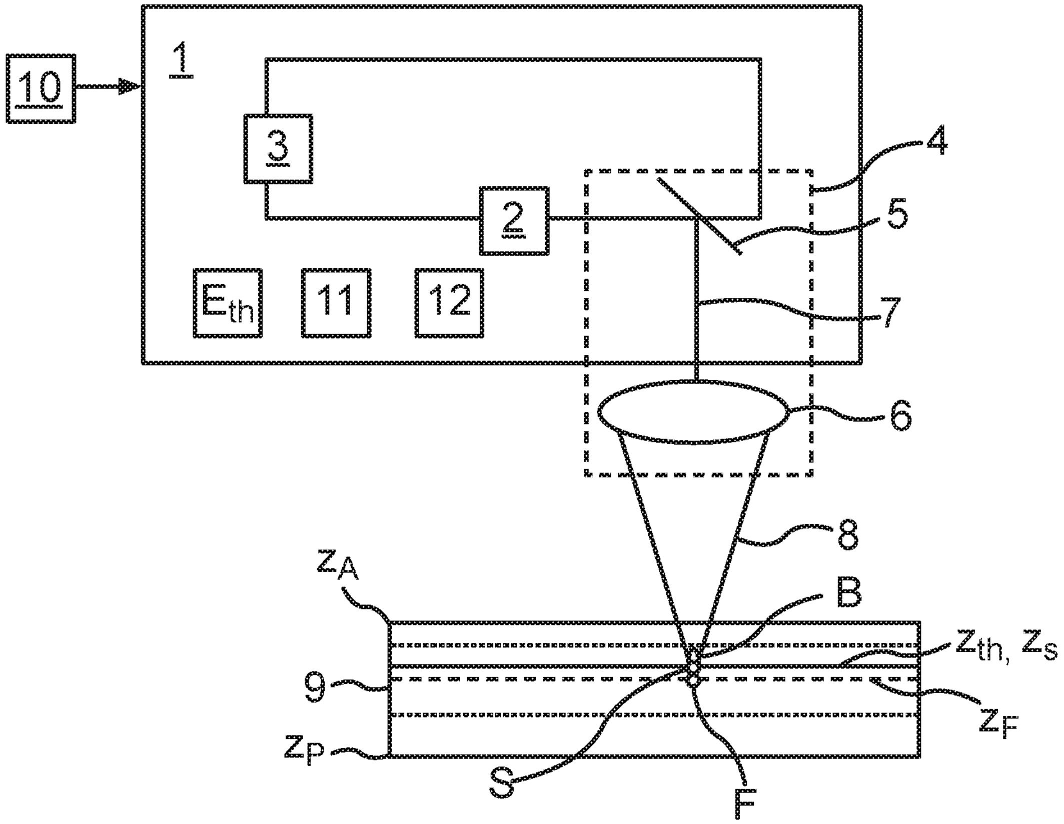
FIG. 1 a schematic representation of a processing device with a laser and focusing optics.

FIG. 1 shows a schematic representation of a processing device with a laser and focusing optics.

A schematic representation of a processing device 1 with a laser 2 for the separation of an object by a predefined material volume of a material 9 with a predefined separation surface in a predetermined separation depth $z_S$ by photodisruption is shown. One recognizes that a control device 3 for the laser 2 may be formed besides the laser 2 such that it emits pulsed laser pulses 7 for example in a predefined pattern to the object, wherein the ascertained interfaces $z_A$ $z_P$ of a lenticule to be formed may be generated by for example a predefined pattern by photodisruption. Alternatively, the control device 3 may be a control device 3 external with respect to the processing device 1.

Furthermore, FIG. 1 shows that the laser pulse 7 generated by the laser 2 is deflected towards a surface $z_A$ of a material 9 by a beam device 4, which includes a beam deflection device 5 such as for example a rotation scanner. The beam deflection device 5 is also controlled by the control device 3 to generate the ascertained interfaces $z_A$ $z_P$, preferably also incisions or cuts, along preset incision courses.

Preferably, the illustrated laser 2 may be a photodisruptive laser, which is formed to emit the laser pulses 7 in a wavelength range between 300 nm and 1400 nm, preferably between 700 nm and 1200 nm, at a respective pulse duration between 1 fs and 1 ns, preferably between 10 fs and 10 ps, and a repetition frequency of greater than 10 kHz, preferably between 100 kHz and 100 MHz. In addition, the control device 3 optionally comprises a storage device (not illustrated) for at least temporary storage of at least one control dataset, wherein the control dataset or datasets include(s) control data for positioning and/or for focusing individual laser pulses 7 in the material 9. The position data and/or focusing data of the individual laser pulses 7, that is the geometry of the material volume to be separated, are ascertained based on the method described below.

The control device 3 may be configured to receive a specification 10 for separating the material 9 by a method based on an optical breakthrough, such as for example the photodisruption, in at least one preset separation point S in a respective, preset separation depth $z_S$ of the material 9. The control device 3 may be configured to control the focusing optics 6 of the processing device 1 by the control data to adjust a focusing depth $z_F$ respectively to be adjusted of a respective focusing point F for separating the material 9 in the respective separation point S in the respective separation depth $z_S$ of the material 9. It may be provided that multiple separation points S are preset along the separation plane in respective separation depths $z_S$ by the specification 10 to detach the material 9 in the separation depth $z_S$. The control device 3 may be configured to ascertain the respective focusing depth $z_P$ to be adjusted of a respective focusing point F for separating the material 9 in the respective separation point S in the preset separation depth $z_S$ according to a predetermined adaptation method. Therein, the separation depth $z_S$ may deviate from the focusing depth $z_F$. The focusing depth $z_F$ may depend on the breakthrough parameter threshold $E_{th}$, which may describe a breakthrough parameter E of the laser pulse 7, which results in an ignition of a plasma in the material 9. The breakthrough parameter E may for example relate to a power, a power density, an energy and/or an energy density. By the ignition of the plasma, the separation or generally a processing of the material 9 may be effected.

The disruption may begin in the breakthrough depth $z_{th}$, in which the breakthrough parameter E of the laser pulse 7 exceeds the breakthrough parameter threshold $E_{th}$. Depending on a numerical aperture, a cross-sectional surface of the laser pulse 7 oriented normally to a direction of the laser pulse 7 may decrease upon passage through the material 9 such that the breakthrough parameter E of the laser pulse 7 may increase with the depth. The depth, in which the breakthrough parameter E exceeds the breakthrough parameter threshold $E_{th}$, characterizes the said breakthrough depth $z_{th}$. In order to be able to ascertain the breakthrough depth $z_{th}$, the adaptation method may consider at least one laser parameter 11, which may for example include the numerical aperture and/or the intensity of the laser pulse. Exceeding the breakthrough parameter threshold $E_{th}$ may also depend on the tissue itself. For this purpose, the control device 3 may be configured to ascertain the breakthrough depth $z_{th}$ depending on at least one material parameter 12. The material parameter 12 may for example describe an absorption capacity of the material 9. The control device 3 may be configured to ascertain the focusing depth $z_F$ to be adjusted for the respective focusing point F, which has to be adjusted to separate the material 9 in the respective separation point S in the respective separation depth $z_S$ of the material 9. For ascertaining the focusing depth $z_F$ in the adaptation method, the control device 3 may be configured to ascertain the focusing depth $z_F$ of the focusing point F by a conversion table. In other words, the conversion table may be stored in the control device 3, from which the control device 3 may read out the focusing depth $z_F$ to be adjusted for the separation depth $z_S$, the breakthrough parameter threshold $E_{th}$, the at least one laser parameter 11 and/or the at least one material parameter 12. Ascertaining the focusing depth $z_F$ may also be effected by a fit function. In other words, a fit function may be stored in the control device 3, from which the focusing depth $z_F$ may be ascertained. The fit function may for example be approximated from simulated or experimentally ascertained focusing depths $z_F$ for certain parameters 11, 12 or separation depths $z_S$. The control device 3 may also be configured to ascertain the focusing depth $z_F$ of the focusing point F by a model.

In other words, the focusing depth $z_F$, which results in the fact that the breakthrough depth $z_{th}$ coincides with the separation depth $z_S$, is ascertained by the control device 3. Thus, the material 9 is severed in the respective separation point S in the preset separation depth $z_S$.

The control device 3 may also be configured to ascertain the breakthrough parameter threshold $E_{th}$ according to a threshold value ascertaining method depending on the at least one laser parameter 11 and/or the at least one material parameter 12. In other words, the control device 3 may be configured to ascertain the breakthrough parameter threshold $E_{th}$, from which a breakthrough reaction of the material 9 begins. In the threshold value ascertaining method, the at least one preset laser parameter 11 and/or the at least one preset material parameter 12 may be taken into account.

Figure 2:
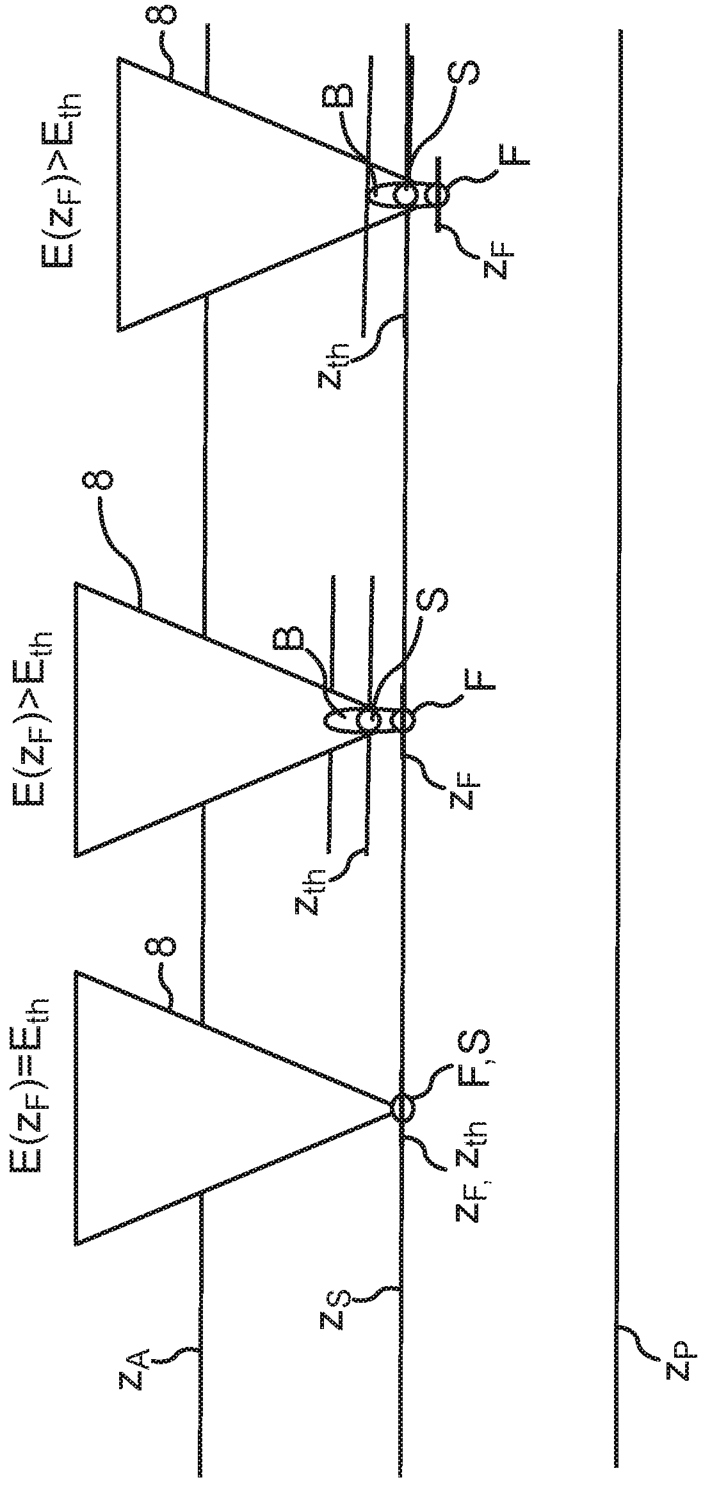
FIG. 2 a schematic representation of a position of the separation plane and the disruption plane.

FIG. 2 shows a schematic representation of a position of the separation plane and the disruption plane.

The situation illustrated on the left shows a case, in which the focusing depth $z_F$ coincides with the separation depth. In other words, the laser pulse is focused on the separation plane. Therein, the breakthrough parameter threshold $E_{th}$ is exceeded in the focusing point F such that the plasma ignition, as preset, is effected in the separation plane.

The central representation shows a laser pulse, which is also focused on the separation plane. However, the breakthrough parameter threshold $E_{th}$ is exceeded in a lower depth in the breakthrough depth $z_{th}$, such that the plasma is ignited above the separation plane. Due to a bubble formation above the separation plane, the material 9 is separated in a lower depth than the separation depth $z_S$.

The right representation shows a laser pulse 7, which is focused on a focusing depth $z_F$ of a focusing point F below the separation depth $z_S$. Therein, the focusing depth $z_F$ was ascertained depending on the breakthrough parameter threshold $E_{th}$ according to the predetermined adaptation method. Therein, the focusing depth $z_F$ was selected such that the breakthrough parameter threshold $E_{th}$ is exceeded in the breakthrough depth $z_{th}$, which coincides with the separation depth $z_S$. Thereby, the beginning of the breakthrough reaction of the material 9 in a lower depth than the focusing depth $z_F$ is compensated for.

Figure 3:
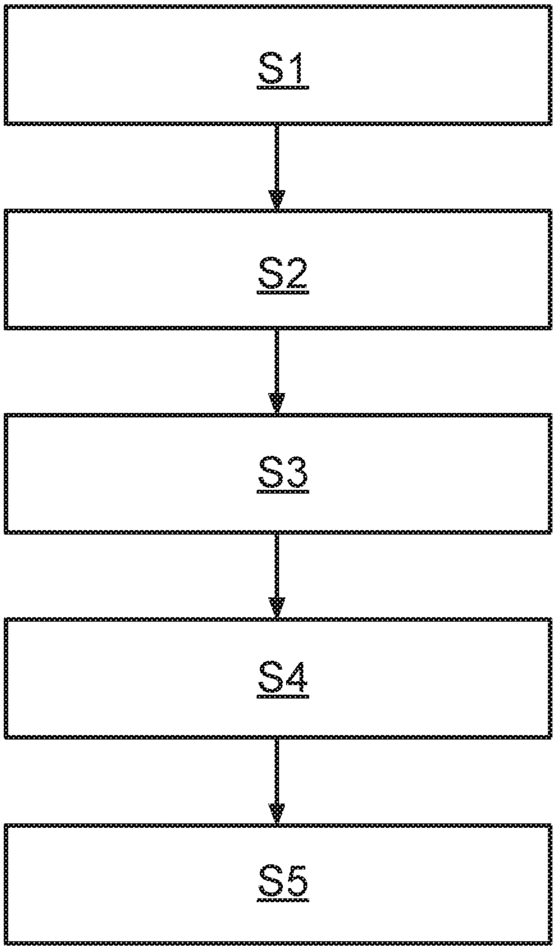
FIG. 3 a schematic representation of a flow of a method for providing control data.

FIG. 3 shows a schematic representation of a flow of a method for providing control data.

In a first step S1, a specification for separating a material 9 of an object by photodisruption in a preset separation point S in a preset separation depth $z_S$ of the material 9 may be received by a control device 3. The preset separation point S may be a position of a predetermined pattern, which is provided in a separation plane $z_S$ of the material 9 to remove a part of the material 9. The separation depth $z_S$ of the preset separation point S may relate to a distance to a surface $z_A$ of the material 9. In a preset separation point S, a bubble is to be formed by at least one laser pulse 7, at which the material 9 is separated.

In a following step S2, a value of a breakthrough parameter threshold $E_{th}$ may be ascertained by the control device 3 according to a predetermined threshold value ascertaining method. The value of the breakthrough parameter threshold $E_{th}$ may describe an energy, an energy density, a power or a power density, from which a breakthrough reaction of the material 9 begins and thus a bubble forms in a breakthrough point B in the material 9. The value of the breakthrough parameter threshold $E_{th}$ may be stored in the control device 3 or be preset to the control device 3. It may be preset that the value of the breakthrough parameter threshold $E_{th}$ is ascertained according to the threshold value ascertaining method depending on at least one preset laser parameter 11 and/or at least one material parameter 12. The at least one preset laser parameter 11 may for example include a wavelength of the laser pulse 7, a pulse duration or an energy of the at least one laser pulse 7. The at least one material parameter 12 may for example include a density and/or a water portion of the material 9. In case of ascertaining the breakthrough parameter threshold $E_{th}$ according to the threshold value ascertaining method depending on the at least one preset laser parameter 11 and/or the at least one material parameter 12, the advantage arises that a more accurate value of the breakthrough parameter threshold $E_{th}$ is provided for the further method than with a statistically preset value of the breakthrough parameter threshold $E_{th}$. This is attributable to the fact that the breakthrough parameter threshold $E_{th}$ is not a constant value, but is influenced both by the laser pulse 7 and by the material 9. Thus, the breakthrough parameter threshold $E_{th}$ may for example depend on a wavelength of the laser pulse 7 and/or a duration of the laser pulse 7. Similarly, an absorption capacity of the material 9 may influence the breakthrough parameter threshold $E_{th}$. Ascertaining the breakthrough parameter threshold $E_{th}$ may for example be effected by a conversion table of a fit function or a model.

In a method step S3, the focusing depth $z_F$ to be adjusted, in which a focusing point F is situated, on which the at least one laser pulse 7 is focused to cause a breakthrough reaction of the material 9 in the preset separation point P in the preset separation depth $z_S$, may be ascertained by the control device 3 according to a predetermined adaptation method. Therein, the focusing depth $z_F$ is selected such that the breakthrough depth $z_{th}$, in which the breakthrough parameter threshold $E_{th}$ is exceeded by the laser pulse 7, coincides with the separation depth $z_S$. While the threshold value ascertaining method is provided for ascertaining the breakthrough parameter threshold $E_{th}$, the adaptation method may be provided for ascertaining the laser course 8 of the at least one laser pulse 7 through the material 9. Therein, it may be taken into account that a width of the at least one laser pulse 7 may decrease with increasing depth in the material 9 and may reach a minimum in the focusing depth $z_F$. With decreasing width, the power density and/or the energy density of the at least one laser pulse 7 may for example increase. The increase may depend on a focusing angle. With the depth z, the breakthrough parameter E, such as for example the energy density and/or the power density, may increase until the breakthrough parameter threshold $E_{th}$ is exceeded in the breakthrough depth $z_{th}$. It may be possible that the breakthrough parameter threshold $E_{th}$ is exceeded in a depth z, which is lower than the focusing depth $z_F$. This results in the disruption beginning above the separation depth $z_S$. In the adaptation method, this deviation may be ascertained and a focusing depth z may be ascertained, which results in the at least one laser pulse 7 exceeding the breakthrough parameter threshold $E_{th}$ in a breakthrough depth $z_B$, which is in the separation depth $z_S$. The position of the breakthrough depth $z_{th}$ may depend on the numerical aperture of the laser pulse 7, the density of the laser pulse 7 or else on the absorption capacity of the material 9.

In a step S4, a focusing optics 6 of the processing device 1 may be controlled by the control device 3 by the control data to focus a focusing of a laser pulse 7 on the focusing point F in the focusing depth $z_F$ to be adjusted.

In a method step S5, a laser of the processing device 1 may be controlled by the control device 3 in order that it outputs the laser pulse 7.

Figure 4:
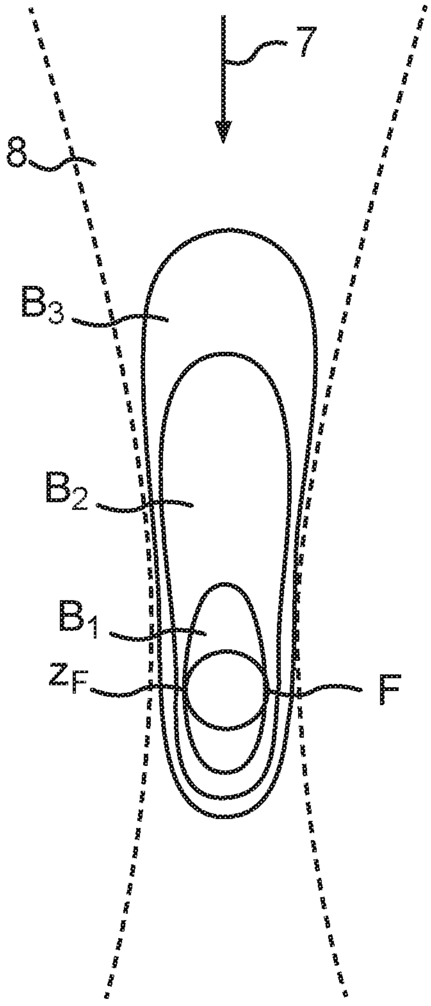
FIG. 4 a schematic representation of disruption bubbles, which form at different laser pulse energies.

FIG. 4 shows a schematic representation of disruption bubbles, which form at different laser pulse energies.

The course of the cross-section of the laser pulse 7 is shown. The laser pulse 7 may be focused on the focusing point F by the focusing optics 6, which may be situated in the focusing depth $z_F$. A first bubble B1 may form by a breakthrough reaction of the material 9 if the laser pulse 7 has a certain laser pulse energy. If the laser pulse 7 has a higher laser pulse energy, a bubble B2 may form by the disruption, wherein the breakthrough parameter threshold $E_{th}$ may be exceeded in a lower depth than the focusing depth $z_F$. With an even higher laser pulse energy, the breakthrough parameter threshold $E_{th}$ may be exceeded in an even lower depth, such that the breakthrough depth $z_B$ may shift upwards with increasing energy of the laser pulse 7 as it is apparent at the bubble B3.

By the provided invention, it is possible both to reduce the deviations of the separation depth from a preset separation depth and to provide a more precisely cut separation surface.

The invention claimed is:

1. A method for providing control data for a processing device with at least one laser and with at least one focusing optics, wherein the method comprises the following steps performed by a control device:

receiving a specification for processing a material of an object in at least one preset separation point in a respective, preset separation depth of the material, ascertaining a respective focusing depth of a focusing point to be adjusted in the at least one focusing optics of the processing device for separating the material in the respective, at least one preset separation point in the preset separation depth of the material, and providing the control data, wherein the control data is configured for controlling the at least one focusing optics of the processing device for focusing at least one laser pulse on the focusing point in the focusing depth of the material to be adjusted and for controlling the at least one laser of the processing device for outputting the at least one laser pulse to the focusing point, characterized in that:

the focusing depth to be adjusted is adjusted according to a predetermined adaptation method depending on a breakthrough parameter threshold, from which a breakthrough reaction of the material begins, at least one laser parameter and/or at least one material parameter, wherein the focusing depth is selected such that the ascertained breakthrough parameter threshold is exceeded by a breakthrough parameter of the at least one laser pulse in a breakthrough depth which coincides with the preset separation depth.

2. The method according to claim 1, wherein the material is a cornea of a human or animal eye.

3. The method according to claim 1, wherein the focusing depth is selected such that the focusing depth is different from the preset separation depth, and the breakthrough parameter of the at least one laser pulse in the preset separation depth is identical to the ascertained breakthrough parameter threshold.

4. The method according to claim 1, wherein the breakthrough parameter threshold is ascertained according to a threshold value ascertaining method depending on the at least one laser parameter and/or the at least one material parameter.

5. The method according to claim 1, wherein the breakthrough parameter describes a local power of the at least one laser pulse and the breakthrough parameter threshold describes a power threshold of the at least one laser pulse, from which the breakthrough reaction of the material begins.

6. The method according to claim 1, wherein the breakthrough parameter describes a local power density of the at least one laser pulse and the breakthrough parameter threshold describes a power density threshold of the at least one laser pulse, from which the breakthrough reaction of the material begins.

7. The method according to claim 1, wherein the breakthrough parameter describes a local energy of the at least one laser pulse and the breakthrough parameter threshold describes an energy threshold of the at least one laser pulse, from which the breakthrough reaction of the material begins.

8. The method according to claim 1, wherein the breakthrough parameter describes a local energy density of the at least one laser pulse and the breakthrough parameter threshold describes an energy density threshold of the at least one laser pulse, from which the breakthrough reaction of the material begins.

9. The method according to claim 1, wherein the at least one laser parameter of the at least one laser pulse includes an energy of the at least one laser pulse.

10. The method according to claim 1, wherein the at least one laser parameter of the at least one laser pulse includes a numerical aperture of the at least one laser pulse.

11. The method according to claim 1, wherein the at least one laser parameter of the at least one laser pulse includes a wavelength of the at least one laser pulse.

12. The method according to claim 1, wherein the at least one laser parameter of the at least one laser pulse includes a pulse duration of the at least one laser pulse.

13. The method according to claim 1, wherein the at least one laser parameter of the at least one laser pulse includes a pulse frequency of consecutive laser pulses.

14. The method according to claim 1, wherein the at least one material parameter includes an absorption coefficient of the material.

15. The method according to claim 1, wherein the predetermined adaptation method includes ascertaining the focusing depth of the respective focusing point by a conversion table.

16. The method according to claim 1, wherein the predetermined adaptation method includes ascertaining the focusing depth of the respective focusing point by a fit function.

17. The method according to claim 1, wherein the predetermined adaptation method includes ascertaining the focusing depth of the respective focusing point by a model.

18. A method for controlling the processing device according to claim 1, wherein the method further comprises the following steps:

transferring the provided control data to a processing device with at least one laser and at least one focusing optics.

19. A control device, which is formed to perform a respective method according to claim 1.

20. A processing device with at least one laser and at least one focusing optics for the separation of a material volume with predefined interfaces of an object by photodisruption, and at least one control device according to claim 19.

21. A non-transitory computer-readable medium configured for storing a computer program, the computer program including commands which cause a control device to execute the method according to claim 1.

* * * * *